United States Patent
Knauf et al.

(10) Patent No.: US 9,845,286 B2
(45) Date of Patent: Dec. 19, 2017

(54) PROCESS FOR OPERATING A GAS PHASE PHOSGENATION PLANT

(71) Applicant: Covestro Deutschland AG, Leverkusen (DE)

(72) Inventors: Thomas Knauf, Dormagen (DE); Wolfgang Lorenz, Dormagen (DE); Friedhelm Steffens, Leverkusen (DE); Rainer Bruns, Bergisch Gladbach (DE); Wolfgang Taube, Neuss (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/127,826

(22) PCT Filed: Mar. 24, 2015

(86) PCT No.: PCT/EP2015/056216
§ 371 (c)(1),
(2) Date: Sep. 21, 2016

(87) PCT Pub. No.: WO2015/144682
PCT Pub. Date: Oct. 1, 2015

(65) Prior Publication Data
US 2017/0096389 A1    Apr. 6, 2017

(30) Foreign Application Priority Data
Mar. 27, 2014 (EP) .................... 14162002

(51) Int. Cl.
| C07C 263/00 | (2006.01) |
| C07C 263/10 | (2006.01) |
| B01J 19/00 | (2006.01) |
| B01J 19/24 | (2006.01) |

(52) U.S. Cl.
CPC ......... *C07C 263/10* (2013.01); *B01J 19/0006* (2013.01); *B01J 19/24* (2013.01); *B01J 2219/00027* (2013.01); *B01J 2219/00164* (2013.01); *B01J 2219/24* (2013.01)

(58) Field of Classification Search
CPC .. C07C 263/10; C07C 265/14; B01J 19/0006; B01J 19/24; B01J 2219/00164; B01J 2219/24; B01J 2219/27; B01J 2219/00027
See application file for complete search history.

(56) References Cited

U.S. PATENT DOCUMENTS

| 5,679,839 | A | 10/1997 | Armand et al. |
| 7,084,297 | B2 | 8/2006 | Woelfert et al. |
| 7,754,915 | B2 | 7/2010 | Herold et al. |
| 7,915,444 | B2 | 3/2011 | Woelfert et al. |
| 8,258,337 | B2 | 9/2012 | Woelfert et al. |
| 8,399,702 | B2 | 3/2013 | Pohl et al. |
| 8,563,768 | B2 * | 10/2013 | Bruns .................... C01B 31/28 560/347 |
| 8,692,016 | B2 | 4/2014 | Sanders et al. |
| 8,779,181 | B2 | 7/2014 | Mattke et al. |
| 9,006,481 | B2 | 4/2015 | Mattke et al. |
| 9,302,983 | B2 | 4/2016 | Lehr et al. |
| 2004/0167354 | A1 * | 8/2004 | Biskup ................ B01F 5/0453 560/336 |
| 2011/0301380 | A1 * | 12/2011 | Knoesche ............ C07C 263/10 560/347 |
| 2012/0095255 | A1 * | 4/2012 | Mattke .................. C07C 263/10 560/347 |
| 2012/0123152 | A1 * | 5/2012 | Bruns .................... C01B 31/28 560/347 |
| 2013/0060062 | A1 * | 3/2013 | Mattke ................ C07C 263/10 560/347 |
| 2015/0291512 | A1 | 10/2015 | Bums et al. |
| 2015/0368190 | A1 | 12/2015 | Steffens et al. |

FOREIGN PATENT DOCUMENTS

| EP | 1371635 A1 | 12/2003 |
| EP | 1371636 A1 | 12/2003 |
| EP | 1413571 A1 | 4/2004 |
| WO | 2013029918 A1 | 3/2013 |

* cited by examiner

*Primary Examiner* — Yevgeny Valenrod
*Assistant Examiner* — Blaine G Doletski
(74) *Attorney, Agent, or Firm* — N. Denise Brown

(57) ABSTRACT

This invention relates to a process for operating a gas phase phosgenation plant (100) to form an isocyanate (4) by reacting an amine (2) with phosgene (1), in which the gas phase phosgenation plant is shut down by first stopping the amine stream and still maintaining the phosgene stream. After a period of time which corresponds to at least 10 times the residence time of phosgene (1) in the main parts of the gas phase phosgenation plant (100) in regular operation, calculated from the time at which the amine inflow has been completely stopped, the feed of phosgene is also stopped. An inert gas stream (3) is maintained through the amine and phosgene feeding devices and through all the other essential parts of the gas phase phosgenation plant (100) during the shutdown.

18 Claims, 3 Drawing Sheets

PROCESS FOR OPERATING A GAS PHASE PHOSGENATION PLANT

CROSS-REFERENCE TO RELATED APPLICATIONS

This application is a National Phase Application of PCT/EP2015/056216, filed Mar. 24, 2015, which claims priority to European Application No. 14162002.1, filed Mar. 27, 2014, each of which being incorporated herein by reference.

FIELD

The invention relates to a method of operating a gas phase phosgenation plant (100) for reacting an amine (2) with phosgene (1) to give the corresponding isocyanate (4), in which the gas phase phosgenation plant (100) is shut down by first stopping the amine stream and still maintaining the phosgene stream. No earlier than after a period corresponding to 10 times, preferably 30 times, more preferably 60 times and most preferably 90 times the residence time of phosgene (1) in the essential sections of the gas phase phosgenation plant (100) in the regular operation thereof has elapsed, calculated from the moment from which the amine feed has been completely stopped, the phosgene supply is also stopped. During the shutdown operation, an inert gas stream (30) is maintained through the amine and phosgene feed devices and through all other essential sections of the gas phase phosgenation plant (100).

BACKGROUND

Isocyanates are produced in large volumes and serve mainly as starting materials for production of polyurethanes. They are usually prepared by reacting the corresponding amines with phosgene, using phosgene in a stoichiometric excess. The reaction of the amines with the phosgene can be effected either in the gas phase or in the liquid phase. It is a feature of the process regime in the gas phase, typically referred to as gas phase phosgenation, that the reaction conditions are chosen such that at least the amine, isocyanate and phosgene reaction components, but preferably all the reactants, products and reaction intermediates, are gaseous under the conditions chosen. Advantages of gas phase phosgenation include reduced occurrence of phosgene (called phosgene "hold-up"), the avoidance of intermediates that are difficult to phosgenate, increased reaction yields and a lower energy requirement, since less solvent is being employed. The present invention relates exclusively to gas phase phosgenation and relates especially to a seamless method of starting up a gas phase phosgenation plant.

The prior art discloses various processes for preparing isocyanates by reacting amines with phosgene in the gas phase. An important factor for a good process regime is good mixing of the reactants of the gas phase phosgenation. EP-A-0 289 840 describes the preparation of diisocyanates by gas phase phosgenation, wherein the preparation in accordance with the invention takes place in a turbulent flow at temperatures between 200° C. and 600° C. in a cylindrical space without moving parts.

EP-A-0 570 799 relates to a process for preparing aromatic diisocyanates, in which the reaction of the corresponding diamine with the phosgene is conducted in a tubular reactor above the boiling temperature of the diamine within a mean contact time of 0.5 to 5 seconds.

EP-A-0 699 657 describes a process for preparing aromatic diisocyanates in the gas phase, in which the reaction of the corresponding diamine with the phosgene takes place in a reactor comprising two zones, wherein the first zone, which makes up about 20% to 80% of the total reactor volume, has ideal mixing and the second zone, which makes up 80% to 20% of the total reactor volume, can be characterized by plug flow. Preferably, the second reaction zone is executed as a tubular reactor.

The optimization of the use of tubular reactors for gas phase phosgenation, the principle of which has been disclosed in EP-A-0 570 799 with use of the jet mixer principle (Chemie-Ing.-Techn. 44 (1972) p. 1055, fig. 10), is the subject of numerous applications.

According to the teaching of EP-A-1 362 847, homogenization of the reactant stream supplied via the ring space of the tubular reactor and very central feeding of the two reactant streams into the tubular reactor have a great positive influence on the stability of the reaction zone and hence on the gas phase reaction overall.

As described in EP-A-1 555 258, enlargement of the tubular reactors used also necessitates enlargement of the mixing nozzle, which frequently takes the form of a smooth jet nozzle. However, the increase in the diameter of the smooth jet nozzle also reduces the speed of mixing of the central jet as a result of the greater diffusion length required and increases the risk of backmixing, which in turn leads to the formation of polymeric impurities and hence of solid material baked onto the reactor. According to the teaching of EP-A-1 555 258, the disadvantages described can be eliminated when one reactant stream is injected at high velocity via a concentric annular gap in the stream of the other reactant. This makes the diffusion length for mixing small and the mixing times very short. The reaction can then proceed with high selectivity to give the desired isocyanate. The occurrence of polymeric impurities and the formation of caked-on material are reduced thereby.

According to the teaching of EP-A-1 526 129, an increase in the turbulence of the reactant stream in the central nozzle has a positive influence on the mixing of the reactants and hence on the gas phase reaction overall. As a result of the better mixing, there is a decrease in the tendency to form by-products.

EP-A-1 449 826 discloses a process for preparing diisocyanates by phosgenation of the corresponding diamines, in which the vaporous diamines, optionally diluted with an inert gas or with the vapors of an inert solvent, and phosgene, are heated separately to temperatures of 200° C. to 600° C. and mixed and reacted in a tubular reactor, wherein a number n≥2 of nozzles aligned parallel to the axis of the tubular reactor are arranged within the tubular reactor, wherein the stream comprising the diamines is fed to the tubular reactor via the n nozzles and the phosgene stream is fed to the tubular reactor via the remaining free space.

A further development of the use of tubular reactors for gas phase phosgenation is the subject of WO 2007/028715. The reactant used has a mixing device and a reaction space. According to the teaching of WO 2007/028715, the reaction space comprises, in the front region, the mixing space in which predominantly the mixing of the gaseous phosgene and amine reactants, optionally mixed with inert medium, takes place, which is generally accompanied by the onset of the reaction. According to the teaching of WO 2007/028715, in the rear part of the reaction space, it is essentially only the reaction that then takes place, and mixing at most to a minor degree. Preferably, in the process disclosed in WO 2007/028715, reaction spaces that are rotationally symmetric with respect to the flow direction are used, it being possible to divide these, in terms of construction, essentially into up to four longitudinal sections along the longitudinal axis of the reactor over the flow profile, the longitudinal sections differing in terms of the size of the cross-sectional flow area.

WO 2008/055898 discloses a process for preparing isocyanates by phosgenation of the corresponding amines in the gas phase in a reactor, in which, analogously to WO 2007/028715, the reactor used has a mixing device and a reaction space, the rotationally symmetric reaction space can be divided, in terms of construction, essentially into up to four longitudinal sections along the longitudinal axis of the reactor over the flow profile, the longitudinal sections differing in terms of the size of the cross-sectional flow area. Compared to WO 2007/028715, the changes in the cross-sectional flow areas, however, are achieved not by means of a voluminous body installed into a tubular reactor but by means of a corresponding extension or constriction of the outer reactor wall.

EP-A-1 275 639 likewise discloses, as a possible process variant for preparation of isocyanates by phosgenation of the corresponding amines with phosgene in the gas phase, the use of a reactor in which the reaction space has, in flow direction, beyond the mixing of the two reactants, an extension of the cross-sectional flow area. By means of a suitably chosen extension of the cross-sectional area, it is possible to keep the flow rate of the reaction mixture over the length of the reactor just constant. This increases the reaction time available with the same reactor length.

EP-A-2 196 455 discloses that phosgene and the primary aromatic amines are converted above the boiling temperature of the amines in a reactor comprising a reaction space which is essentially rotationally symmetric with respect to the flow direction, wherein the cross-sectional average flow rate of the reaction mixture along the axis of the essentially rotationally symmetric reaction space in the section of the reaction space in which the conversion of the amino groups to the isocyanate groups is between 4% and 80% is not more than 8 m/sec and wherein the cross-sectional average flow rate of the reaction mixture along the axis of the essentially rotationally symmetric reaction space in this section of the reaction space is always below the cross-sectional average flow rate at the start of this section.

EP-A-1 935 876 discloses a gas phase process for preparing isocyanates by reacting corresponding primary amines with phosgene, in which phosgene and the primary amines are converted above the boiling temperature of the amines within a mean contact time of 0.05 to 15 seconds, the conversion being conducted adiabatically.

EP-A-2 408 738 discloses how a dissociation of phosgene to chlorine and carbon monoxide as a result of an excessively long residence time of the phosgene-containing streams at high temperature can be avoided. By reduction of the residence time of the phosgene at temperatures greater than 300° C. to a maximum of 5 s and by the limitation of the temperature of the heat transfer areas in contact with phosgene of not more than 20 K above the phosgene temperature to be established, this is said to be avoided.

EP-B-1 935 875 discloses a process for preparing isocyanates by reacting corresponding primary amines with phosgene in the gas phase, in which the reaction is stopped by conducting the reaction mixture out of the reaction space through a cooling zone into which liquids are injected, the direct cooling in the cooling zone being effected in one stage in two or more cooling zones connected in series (called "quenching" of the reaction mixture).

WO 2013/029918 describes a process for preparing isocyanates by reacting the corresponding amines with phosgene, which can also be conducted at different loads on the gas phase plant without any problems, and more particularly, even when running the plant in the partial load range, the mixing and/or the reaction is said to proceed within the optimized residence time window in each case, by increasing the ratio of phosgene to amine or adding one or more inert substances to the phosgene and/or amine stream. The method of the invention is to enable operation of an existing plant at different loads with constant product and process quality. This is to dispense with the provision of several plants with different nameplate capacities.

The application teaches that essential parameters of a phosgenation, such as the residence times of the co-reactants in the individual apparatuses in particular, are optimized for the operation of the production plant at nameplate capacity, which can lead to problems in terms of yield and product purity when the plant is operated at lower than nameplate capacity (cf. page 2 lines 20 to 36). In order to be able to attain the optimized—narrow—residence time window even at partial load (i.e. reduced amine flow rate compared to operation at nameplate capacity), it is suggested that either the phosgene stream and/or the inert fraction be increased (cf. page 3 lines 5 to 19), preferably in such a way that the total flow rate of all components corresponds essentially to that at nameplate capacity (cf. page 6 lines 4 to 8). The application does mention shut down operations in the description of the background of the invention claimed on page 2, but does not disclose any technical teaching at all as to the specific way in which a production plant in operation is most advantageously shut down (i.e. amine flow rate and phosgene flow rate are equal to zero). The technical measures disclosed in the application (i.e. the increase in the phosgene flow rate and/or the inert fraction) should be considered exclusively in the context of the problem of operation of a production plant at lower than nameplate capacity, and with the problem of how a plant operated at nameplate capacity can advantageously be switched to operation (i.e. amine and phosgene flow rate significantly greater than zero) at lower than nameplate capacity (see the examples).

Although the prior art processes described succeed in conducting a phosgenation without loss of quality in the end products, the only processes described, with a few exceptions, are those in the normal state of operation. There is no description of the shutdown operation, i.e. the safe shutdown of a gas phase phosgenation plant in a manner which enables seamless restarting at a later time.

The person skilled in the art is aware that such a continuously operated industrial process should not unnecessarily be abruptly shut down. The shutdown of a gas phase phosgenation plant is a frequent everyday industrial operation which need not necessarily be combined with opening or another mechanical intervention into the phosgenation plant. In practice, it is a feature of shutdown that there may be deviations in the excess of phosgene relative to amine compared to the continuous operation at the target nameplate capacity of the production plant. Such deviations occur particularly when, for example, pressure variations result in backmixing. This is observed especially when the current flow rate of amine to be converted is very small compared to the target flow rate of amine to be converted at the target nameplate capacity of the plant. These quantitative variations in the ratio of phosgene to amine are disadvantageous since solids such as polyurea or amine hydrochlorides can precipitate out. Furthermore, in the event of improper shutdown, there can be unwanted formation of droplets of amine. The shutdown of a gas phase phosgenation plant is therefore a critical process step, since errors here can seriously disrupt the later restart and the actual continuous production (for example as a result of an increase in the pressure differential needed to assure a sufficient flow rate of the reactants and products through the plant).

SUMMARY

In spite of the various advances in the field of gas phase phosgenation, there was therefore a need for further improvements. Taking account of this need, the present invention provides a method of operating a gas phase phosgenation plant (100) for reacting an amine (2) with phosgene (1) in a stoichiometric excess in relation to the primary amino groups of the amine (2) to give the corresponding isocyanate (4), said gas phase phosgenation plant (100) comprising at least
(i) an apparatus 1000 for providing a gaseous phosgene stream (10), optionally comprising, as well as phosgene (1), an inert substance (3),
(ii) an apparatus 2000 for providing a gaseous amine stream (20), optionally comprising, as well as amine (2), an inert substance (3),
(iii) a mixing zone (3100) for mixing the streams 10 and 20, the mixing zone being connected by each of devices (1100, 2100) to the apparatus 1000 and the apparatus 2000,
(iv) a reaction zone (3200) arranged downstream of the mixing zone (3100) for further conversion of the previously mixed streams 10 and 20,
(v) a reaction stopping zone (4000) arranged downstream of the reaction zone (3200) to end the reaction,
and optionally
(vi) a workup section (5000) comprising devices for recovery and recycling of unconverted phosgene (1") (5100) and devices for obtaining the isocyanate prepared in pure form (5200),
in which, in the regular operation of the gas phase phosgenation plant (100), the phosgene (1) in the phosgene gas stream (10) is preferably a mixture of fresh phosgene (1') and the devices 5100 recovered recycled phosgene (1"), wherein
the gas phase phosgenation plant (100) is shut down by running the following steps:
(I) reducing the amine mass flow rate M'(2) to zero, while maintaining a gaseous inert gas stream (30) through the device 2100, the mixing zone (3100), the reaction zone (3200) and the reaction stopping zone (4000);
(II) only after a period corresponding to at least 10 times the residence time, preferably at least 30 times the residence time, more preferably at least 60 times the residence time and most preferably at least 90 times the residence time of phosgene (1) from exit from the apparatus 1000 to exit from the reaction stopping zone (4000) in the regular operation of the gas phase phosgenation plant (100) has elapsed, calculated from the moment from which M'(2) is zero, reducing the mass flow rate of phosgene M'(1) leaving the apparatus 1000 to zero, while maintaining a gaseous inert gas stream (30) through the device 1100, the mixing zone (3100), the reaction zone (3200) and the reaction stopping zone (4000);
(III) maintaining at least the inert gas stream (30) from (I), preferably the inert gas streams (30) from (I) and (II), at least for a period corresponding to three times, preferably at least 100 times, more preferably at least 200 times and most preferably at least 350 times the residence time of the inert gas stream (30) from entry into the mixing zone (3100) to exit from the reaction stopping zone (4000), calculated from the moment from which the mass flow rate of phosgene M'(1) leaving the apparatus 1000 is zero.

DETAILED DESCRIPTION

Figure 1:
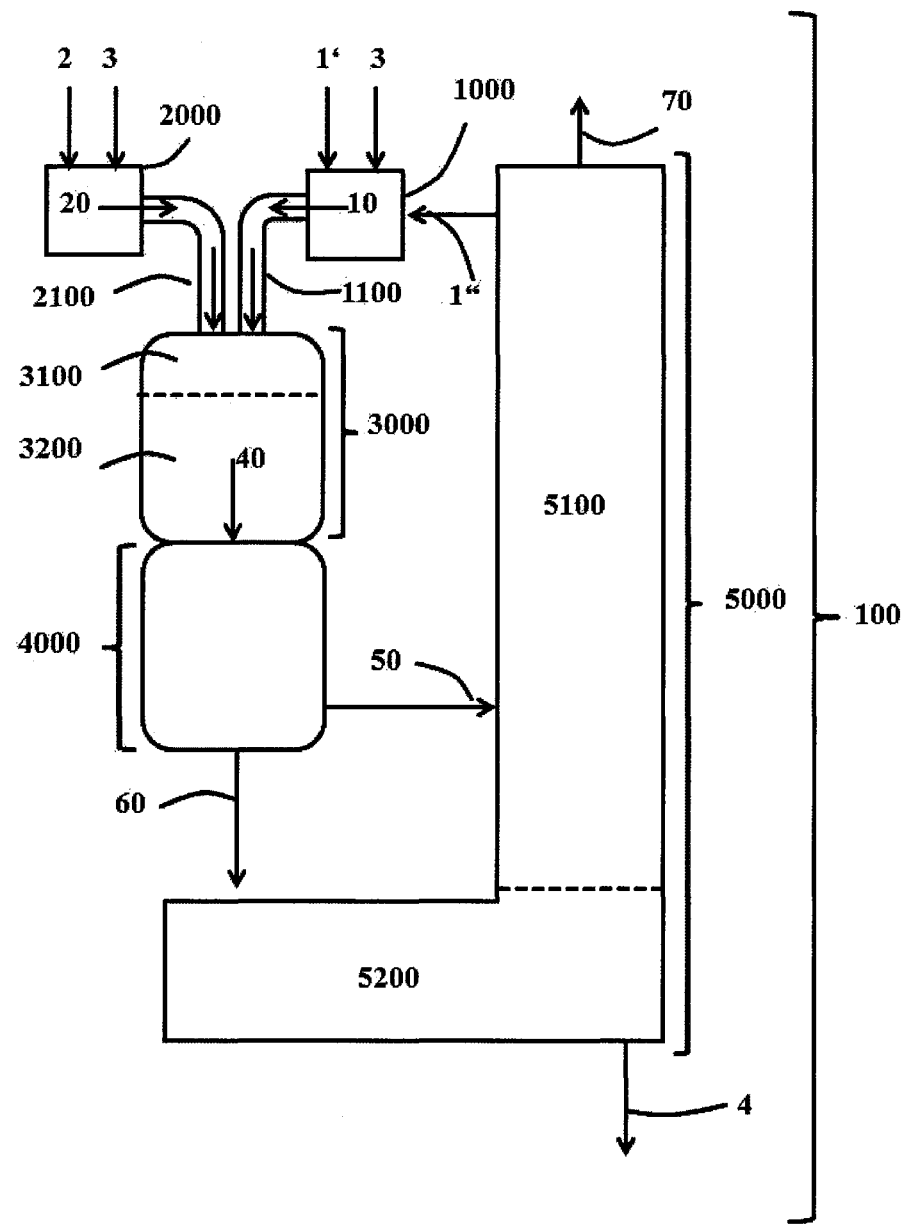
FIG. 1 shows the overall concept of the method according to the invention in which an isocyanate (4) is formed by reacting an amine (2) with a stoichiometric excess of phosgene (1) in relation to the primary amino groups of the amine (2) by which the gas phase phosgenation plant (100) is shut down.

A gas phase phosgenation is understood in accordance with the invention to mean a process regime for phosgenation of amines to the corresponding isocyanates in which the amines in the gaseous state react to give the isocyanates and, in the course of the reaction, all the components present (reactants, products, intermediates, any by-products, any inert substances) remain in the gas phase during passage through the reaction zone to an extent of at least 95.0% by mass, preferably to an extent of at least 98.0% by mass, more preferably to an extent of at least 99.0% by mass, even more preferably to an extent of at least 99.8% by mass and especially to an extent of at least 99.9% by mass, based in each case on the total mass of all the components present.

The residence time of a component in a plant section refers to the quotient of volume flow rate of the component in the standard state (reported as $V_n$/h, where $V_n$ represents $m^3$ under standard conditions ("standard cubic meters")) and the internal flow volume of the plant section in question (reported in $m^3$). A standard cubic meter $V_n$ is that gas volume which, at
a pressure $p_n$ of 1.01325 bar,
an air humidity of 0% (dry gas) and
a temperature $T_n$ of 273.15 K ($t_n$=0° C.) (standard conditions in accordance with DIN 1343, STPD),
would have a volume V of one cubic meter.

The residence time of phosgene (1) in the regular operation of the gas phase phosgenation plant (100), which is relevant in step (II), is a calculated parameter which is determined from the known volume flow rate of phosgene leaving the apparatus 1000 in regular operation (without any inert substance component present) and the known internal volume of the apparatuses through which the material flows, including the pipelines that connect them. In an analogous manner, the residence time of the inert gas stream (30), which is relevant in step (III), is determined by calculation. This is based on the volume flow rate of inert gas stream (30) present at the time at which the mass flow rate M'(1) leaving the apparatus 1000 reaches zero. In the simplest embodiment, this inert gas stream (30) consists of the inert gas stream from (I). Preferably, however, in (III), the inert gas stream from (II) is still maintained. In this latter embodiment, the inert gas stream in (III) therefore consists of the combined inert gas streams from (I) and (II).

Suitable amines (2) are especially isophoronediamine, hexamethylenediamine, bis(p-aminocyclohexyl)methane, tolylenediamine and diphenylmethanediamine.

In the context of the present invention, the expression "shutdown of a gas phase phosgenation plant" encompasses all the process steps required to shut down a gas phase phosgenation plant in operation (which is being operated with a target production at a particular time, expressed as target mass flow rate of the amine to be converted, $M'_{target}$ (2) [e.g. t(amine)/h]), for example in order to conduct maintenance operations. The operation of the gas phase production plant (100) at $M'_{target}(2)$ is referred to in the context of this invention as regular operation. $M'_{target}(2)$ can, but need not, correspond to the value of $M'_{target}(2)$ at nameplate capacity $M'_{nameplate}(2)$ of the gas phase production plant (100). The nameplate capacity of a production plant is reported in the specialist field as tonnes of product to be produced per year ("tonnes per annum"), taking account of all planned plant shutdowns.

The word "a" in the context of this invention, in connection with countable parameters, should be understood merely as the indefinite article and only as the number "one" when this is stated explicitly, for instance by the addition "exactly one". For example, the expression "a reaction zone" does not rule out the possibility of the presence of two or more reaction zones (connected in series or parallel).

It is essential to the invention that, for shutdown of the gas phase phosgenation plant (100), at first only the amine mass flow rate $M'(2)$ is reduced from the value $M'_{target}(2)$ to zero. In the shutdown operation, the amine is always shut down before the phosgene, which prevents backmixing of amine into the phosgene supply devices and assures an excess of phosgene over amine even during the shutdown of the gas phase phosgenation plant (100). The inventive purging of the amine supply devices with an inert gas stream (30) prevents backflow of phosgene into the amine supply devices (backmixing). The purging of the device 2100 (and preferably also of the device 1100), of the mixing zone (3100), of the reaction zone (3200) and of the reaction stopping zone (4000) with an inert gas stream (30) is stopped no earlier than after a period corresponding to three times, preferably 100 times, more preferably 200 times and most preferably 350 times the residence time of the inert gas stream (30) from (I), and in the preferred embodiment that of the combined inert gas streams (30) composed of (I) and (II), from the start of the mixing zone (3100) to exit from the reaction stopping zone (4000), calculated from the moment from which the mass flow rate of phosgene $M'(1)$ leaving the apparatus 1000 is zero.

The steps of the invention are elucidated in detail hereinafter. Various embodiments can be combined here with one another as desired, unless the opposite is apparent to the person skilled in the art from the context.

According to the invention, a gas phase phosgenation plant (100) comprises at least the devices listed above as (i) to (v) (cf. also FIG. 1, which shows the devices of a gas phase phosgenation plant (100) to be used in accordance with the invention, including the workup section which is preferably present and the streams in regular operation).

(i) As apparatus for provision of a gaseous phosgene stream (1000), it is possible in principle to use any apparatus which is known from the prior art and is suitable for the conversion of phosgene to the gas phase. Preferably, the phosgene gas is generated by distillation or partial evaporation in a distillation column, as described in DE102009032413A1 in paragraphs [0081] to [0118]. The energy can be supplied in the bottom of the column by any conceivable evaporator, for example a natural circulation evaporator, climbing film evaporator and falling film evaporator. Falling film evaporators are especially preferred.

(ii) As apparatus for provision of a gaseous amine stream (2000), it is possible in principle to use any apparatus which is known from the prior art and is suitable for the conversion of an amine to the gas phase, such as evaporation apparatuses known to those skilled in the art. In a preferred embodiment, the apparatus 2000 comprises a device for evaporation and a device for subsequent superheating of the amine (2). Very particular preference is given to multistage evaporation and superheating systems in which droplet separators are installed between the evaporation and superheating systems and/or the evaporation apparatuses also have the function of a droplet separator. Suitable droplet separators are described, for example, in "Droplet Separation", A. Bürkholz, VCH Verlagsgesellschaft, Weinheim—New York—Basle—Cambridge, 1989. After leaving the last superheater in flow direction, the gaseous reactant stream (20) preheated to its target temperature is fed to the reaction space.

(iii) A mixing zone (3100) usable in accordance with the invention can be constructed in a manner known to those skilled in the art, preferably as described in EP-A-2 196 455, especially in paragraphs [0047] to [0049], and EP-A-1 935 876, especially in paragraphs [0027] to [0029]. The mixing zone begins where, in regular operation, the streams (10) and (20) meet one another for the first time. At this point, also referred to as entry into the mixing zone (3100), during the shutdown operation, after initiation of step (II), the inert gas streams from (I) and (II) are mixed to give a common inert gas stream, the residence time of which before exit from the reaction stopping zone (4000) forms the basis for the calculation of the minimum duration of step (III).

(iv) The amine and phosgene gas streams that meet one another for the first time in the mixing zone (3100) are converted further in a delay apparatus, the reaction zone (3200). Mixing zone (3100) and reaction zone (3200) can preferably also be combined in a single apparatus, the reactor (3000), as described in EP 2 196 455 A1, especially in paragraphs [0042] to [0049].

Figure 2:
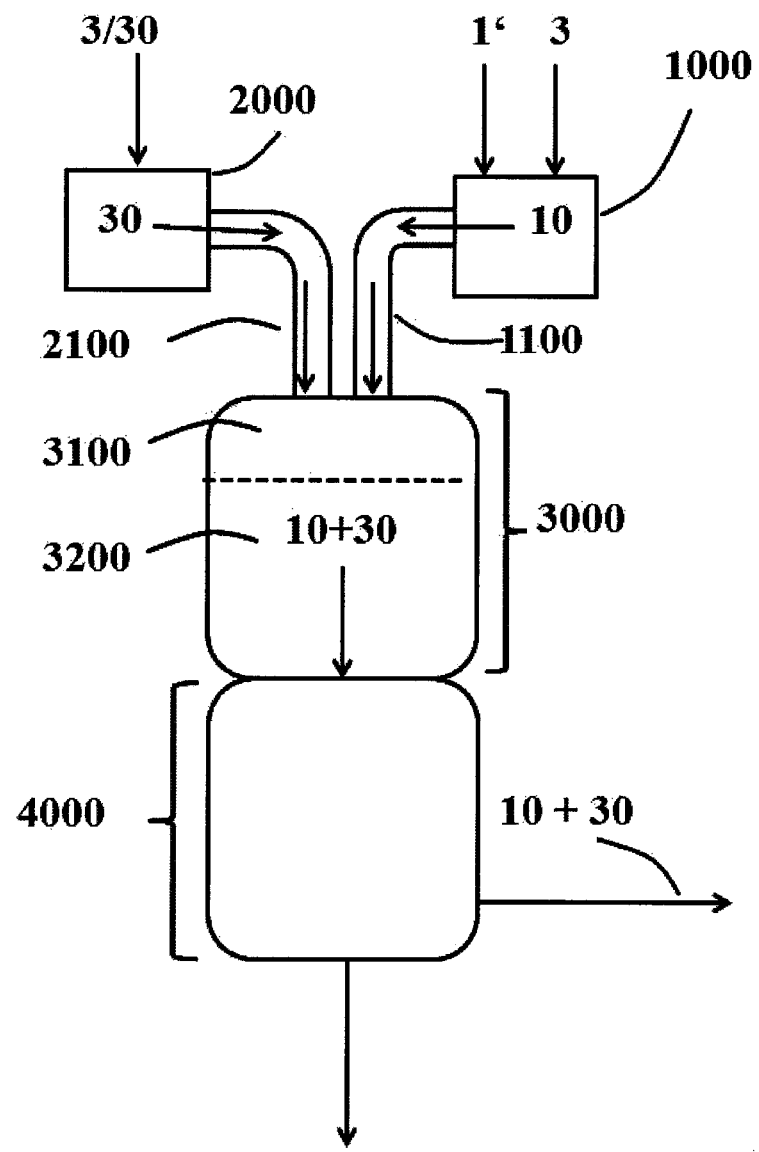
FIG. 2 shows a method according to the invention in which an isocyanate (4) is formed by reacting an amine (2) with a stoichiometric excess of phosgene (1) in relation to the primary amino groups of the amine (2) by which the gas phase phosgenation plant (100) is shut down.

The devices 1100 and 2100 which connect the apparatuses for provision of the gaseous phosgene gas stream (1000) and amine gas stream (2000) to the mixing zone (3100), in accordance with the invention, are those devices which are suitable for transfer of the respective gas stream (10) or (20) from the apparatuses 1000 and 2000 into the mixing zone (3100). These devices comprise, as well as pipelines for transport of the gas streams, preferably also nozzle apparatuses which assure intensive mixing of phosgene gas stream (10) and amine gas stream (20) in the mixing zone (3100). It is possible to inject each of gas streams (10) and (20) individually into the mixing zone (3100). However, preference is given to an embodiment in which the pipelines of the devices 1100 and 2100 open into a common nozzle apparatus (not shown in FIG. 1). In this embodiment, one of the two gas streams, preferably the amine gas stream (20), is supplied to the mixing zone (3100) via an internal nozzle arranged centrally in a preferably cylindrical vessel. The other gas stream, preferably the phosgene gas stream (10) is introduced via the annular space formed by the outer wall of the inner nozzle and the inner wall of the vessel. The two gas streams mix at the exit orifice of the inner nozzle (=start of the mixing zone). Such an embodiment is shown, for example, in FIG. 1 of EP-A-1 449 826. In this case, the devices 1100 and 2100 are partly integrated into one another and into the mixing zone (3100). It is also possible, as shown in FIG. 2 of EP-A-1 449 826, to use an arrangement composed of several individual nozzles in place of a single central nozzle. Further embodiments usable in accordance with the invention for the devices 1100 and 2100 are described, for example, in EP-A-2 196 455, especially in paragraphs [0047] to [0048], and EP-A-1 935 876, especially in paragraphs [0027] and [0028].

(v) Reaction stopping zones (4000) usable in accordance with the invention are known to those skilled in the art. Preference is given to an embodiment as described in EP 1 935 875 B1, especially in paragraphs [0024] and [0025]. In the reaction stopping zone (4000), the crude product of the reaction (40) comprising, as well as the isocyanate (4), essentially also the hydrogen chloride coproduct and unconverted phosgene is cooled rapidly, preferably by injecting an inert solvent (preferably ortho-dichlorobenzene, ODB), optionally together with a portion of previously formed and recycled isocyanate (4), into the gas stream (40). Preferably, the crude reaction product (40) is separated in the reaction stopping zone into a gaseous component (vapor, 50) and a liquid component (60). Preferably, the reaction stopping zone is taken out of operation no earlier than when the mass flow rate of phosgene M'(1) leaving the apparatus 1000 is zero. More preferably, the reaction stopping zone is only after a period corresponding to three times, preferably at least 100 times, more preferably at least 200 times and most preferably at least 350 times the residence time of the inert gas stream (30) from entry into the mixing zone (3100) to exit from the reaction stopping zone (4000), calculated from the moment from which the mass flow rate of phosgene M'(1) leaving the apparatus 1000 is zero.

In a particularly preferred configuration of the method of the invention, the crude product obtained in the reaction stopping zone (4000) is worked up in the same gas phase phosgenation plant (100) in order to isolate the isocyanate (4) from the liquid mixture (60). In this case, the gas phase phosgenation plant (100) additionally comprises (vi) a workup section (5000).

Suitable apparatuses for workup are described in WO 2011/003532, especially page 5 line 19 to page 28 line 5, and in EP 1 371 636 B1, EP 1 371 635 B1 and EP 1 413 571 B1, the whole document in each case. The workup section (5000) can be divided into devices for recovering and recycling unconverted phosgene (and for removing the hydrogen chloride coproduct) (5100) and devices for obtaining the isocyanate prepared in pure form (and optionally for recycling inert solvent) (5200). The workup section is indicated merely schematically in FIG. 1 without the details given hereinafter. More particularly, the workup section (5000) comprises, in the devices 5100, a scrubbing column (5110) for removing isocyanate from the vapors (50) from the reaction stopping zone (4000) by scrubbing with an inert solvent, a phosgene absorption column (5120) for recovering phosgene from the vapors from the scrubbing column (5110) by absorption in an inert solvent, which results in separation of hydrogen chloride and inerts (70) from the phosgene, a phosgene desorption column (5130) for separation of phosgene and inert solvent, and, in the devices 5200, a solvent column (5210), especially for removal of low boilers (especially inert solvent from the reaction stopping zone) from the crude isocyanate, a fine purification column (5220), especially for removal of high boilers (e.g. polyurea-containing residues) from the isocyanate prepurified in the solvent column, such that purified end product is obtained.

It is possible (not shown in FIG. 1) to integrate the apparatus (1000) for provision of a gaseous phosgene stream (10) into the phosgene desorption column (5130) in such a way that the solvent-containing phosgene stream originating from the workup is evaporated together with fresh phosgene (1') and distilled in the phosgene desorption column (5130). The gaseous phosgene obtained is fed to the mixing zone via the device 1100, while the inert solvent removed is preferably conducted into the scrubbing column (5110) and/or the phosgene absorption column (5120).

In the course of operation of the gas phase phosgenation plant (100) with the desired target mass flow rate of amine to be converted of $M'_{target}(2)$, the compositions and mass flow rates of the streams 10 and 20 are preferably matched to one another such that, in stream 10, phosgene (1) is present in a stoichiometric excess in relation to the primary amino groups of the amine (2) in stream 20 of at least 150% of theory, more preferably 160% to 350% of theory and most preferably 170% to 300% of theory. Theoretically, one mole of phosgene reacts with one mole of amino groups, meaning that two moles of phosgene theoretically react with one mole of a diamine. The desired target mass flow rate $M'_{target}(2)$ may correspond to the nameplate capacity of the gas phase phosgenation plant on the basis of a typical plant availability, i.e. the amount of isocyanate produced within a particular period for which the plant has been constructed (generally reported as tonnes per annum). If necessitated by unfavorable sales conditions, the desired target mass flow rate $M'_{target}(2)$ can of course also be lower. This is not essential to the method of the invention. For example, it is entirely conceivable to apply the method of the invention to a gas phase production plant (100) which is being operated temporarily only at 50% of the nameplate capacity because of a difficult market environment. For the duration of the difficult market situation, the regular operation of production then corresponds to an amine mass flow rate $M'_{target}(2) = 0.5 \cdot M'_{nameplate}(2)$.

The gaseous phosgene stream (10) may, as well as phosgene (1), also contain an inert substance (3). Inert substances (3) usable in accordance with the invention are, as well as those substances that are already gaseous at room temperature and standard pressure, such as nitrogen, helium or argon, also the vapors of inert organic solvents that are liquid at room temperature and standard pressure, for example aromatic hydrocarbons, optionally having halogen substitution, for example, chlorobenzene or dichlorobenzene (all isomers, preferably ortho-dichlorobenzene). Particular preference is given to using nitrogen to dilute the phosgene. The proportion of inert substance (3) in the phosgene gas stream (10) may be chosen in the manner customary in the prior art.

It is likewise possible for the gaseous amine stream (20), as well as amine (2), to also contain an inert substance (3). In this case, the same inert substances (3) as described above for the phosgene gas stream (10) are possible. If both streams (10 and 20) contain an inert substance (3), preference is given to using the same inert substance (3).

The operation of the gas phase phosgenation plant (100) at a desired value for the target mass flow rate $M'_{target}(2)$ can be effected by a method known from the prior art. Preferably, for this purpose, the reaction mixture produced in the mixing zone (3100), with avoidance of backmixing, is guided continuously through the reaction zone (3200) and converted therein, preferably at a temperature of 200° C. to 600° C. and an absolute pressure of 80 mbar to 2500 mbar within a mean contact time of 0.05 to 15 seconds, in an adiabatic or isothermal manner, preferably in an adiabatic manner, to a gaseous process product comprising the desired isocyanate (4). Suitable embodiments are described in EP 2 196 455 B1 and EP 1 935 876 B1.

In the reaction stopping zone (4000), the gaseous process product (40) exiting from the reaction zone (3200) is cooled rapidly. This is preferably accomplished by contacting with an inert solvent, the temperature of which is kept below the boiling temperature of isocyanate (4) and above the decomposition temperature of the carbamoyl chloride corresponding to the amine converted. Suitable embodiments are described in EP 1 935 875 B1. Any isocyanate (4) not condensed in this step is preferably removed from the gas mixture remaining in the reaction stopping zone by scrubbing with a scrubbing liquid and preferably combined with the condensate (60) obtained in the reaction stopping zone (4000). A suitable embodiment is described in EP 1 935 875 B1, especially in paragraphs [0024] and [0025].

Thereafter, the desired isocyanate (4) is isolated by distillation from the crude liquid process product (60) thus obtained. Suitable embodiments are known to those skilled in the art and are described, for example, in WO 2013/139703, EP 1 413 571 B1, EP 1 371 635 B1, EP 1 371 636 B1.

The majority of the phosgene unconverted in the reaction remains in the gas phase (50) which is obtained in the reaction stopping zone (4000). It is preferable to work up this gas phase in the devices 5100 of the workup section 5000 which is preferably present, in order to be able to recycle this phosgene. This step is sufficiently well known from the prior art. Suitable embodiments have already been described further up.

To shut down a gas phase phosgenation plant operated in such a way, the following steps are run in accordance with the invention:

In step (I) of the method of the invention, the amine supply into the mixing and reaction zone is shut down. This is accomplished by reducing the amine mass flow rate M'(2) introduced into the apparatus 2000 from the value $M'_{target}(2)$ to zero. This reduction is effected continuously or in stages, preferably continuously. During this step (I), an inert gas stream (30) is maintained through the device 2100, the mixing zone (3100), the reaction zone (3200) and the reaction stopping zone (4000) (cf. also FIG. 2). The inert gas stream (30) consists of at least one inert substance (3), suitable inert substances being the same as described further up for the optional dilution of the phosgene in the gas stream (10). Preferably, this inert gas stream (30) has a temperature above the dew point of the amine (2) under the existing pressure conditions. Preferably, however, the temperature is not so high that there would be any risk of thermal decomposition of the reactants or products still present in the apparatuses. Preference is given in accordance with the invention to a temperature in the range from 200° C. to 600° C., more preferably in the range from 200° C. to 500° C. and most preferably in the range from 250° C. to 500° C.

The maintenance of the inert gas stream (30) in step (I) can be accomplished by (a) introducing an inert substance (3) which is preferably liquid at room temperature and standard pressure at a temperature $T_3$ less than the temperature desired for the inert gas stream (30) in step (I) (i.e. preferably less than 200° C.) into the apparatus 2000, heating it therein and then guiding it into the device 2100 and the further plant sections to be inertized. In variant (a), the inert gas stream (30) is thus provided in the apparatus 2000. This embodiment is advantageous especially when the reaction mixture is diluted during the reaction in regular operation with the vapors of an inert substance (3) which is liquid at room temperature and standard pressure. It is possible to introduce the inert substance (3) in liquid form into the apparatus 2000 and to evaporate it only once therein. Inert substances (3) that are particularly suitable in variant (a) are inert solvent such as aromatic hydrocarbons, optionally having halogen substitution, for example chlorobenzene or dichlorobenzene (all isomers, preferably ortho-dichlorobenzene). In the apparatus 2000, the inert substance (3) is heated (i.e. evaporated in the case of introduction as a liquid) so as to obtain an inert gas stream (30) having a temperature $T_{30}$ of preferably 200° C. to 600° C., more preferably 200° C. to 500° C. and most preferably 250° C. to 500° C., and an absolute pressure $p_{30}$ of preferably 100 mbar to 3000 bar, more preferably 150 mbar to 2800 mbar and most preferably 200 mbar to 2500 mbar. The streams (3) and (30) do not differ in terms of chemical composition, but differ merely in terms of temperature and optionally pressure. After the stream (3) introduced into the apparatus 2000 has been heated, such that it leaves the apparatus 2000 in gaseous form, it is referred to as stream (30).

It is also possible (b) to introduce an inert gas stream (30) at a temperature $T_{30}$ of preferably 200° C. to 600° C., more preferably 200° C. to 500° C. and most preferably 250° C. to 500° C., and an absolute pressure $p_{30}$ of preferably 100 mbar to 3000 mbar, more preferably 150 mbar to 2800 mbar and most preferably 200 mbar to 2500 mbar, directly into the apparatus 2000 and thence to transfer it into the device 2100 and the other plant sections to be inertized. In this embodiment, it is also possible to heat up the inert gas stream (30) introduced further in the apparatus 2000 within the scope of the above-defined temperature ranges. Alternatively, the inert gas stream (30) can also be fed directly into the device 2100. In this latter embodiment, preferably after reducing the mass flow rate of amine M'(2) to zero, the pipeline between the apparatus 2000 and the mixing zone (3100), which is part of the device 2100, is closed, especially preferably immediately beyond the apparatus 2000. Variant (a), no matter what the configuration, is especially advantageous when the reaction mixture, during the reaction in regular operation, is being diluted with an inert substance already in gaseous form at room temperature and standard pressure, such as nitrogen, helium or argon.

Until the complete stoppage of the supply of amine (2) from the apparatus 2000, the pressure in the apparatus 2000 $p_{2000}$ is preferably adjusted by feeding in the inert substance stream (30) to a value above the pressure $p_{3100}$ in the mixing zone (3100). In this case, the value of $p_{3100}$ is preferably 80 mbar (absolute) to 2500 mbar (absolute), while the value $p_{2000}$ is preferably 100 mbar (absolute) to 3000 mbar (absolute).

Figure 3:
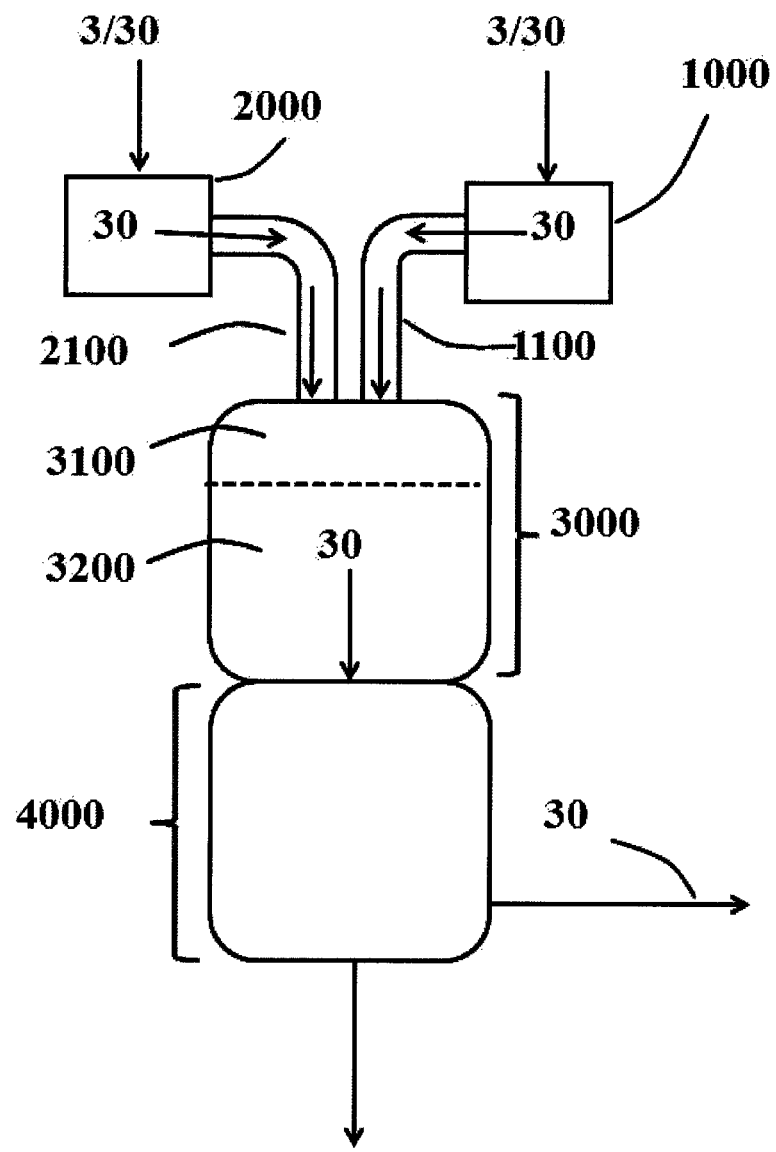
FIG. 3 shows a method according to the invention in which an isocyanate (4) is formed by reacting an amine (2) with a stoichiometric excess of phosgene (1) in relation to the primary amino groups of the amine (2) by which the gas phase phosgenation plant (100) is shut down.

In step (II) of the method of the invention, the mass flow rate of phosgene M'(1) leaving the apparatus 1000 is reduced from the value $M'_{target}(1)$ to zero. This is accomplished continuously or in stages, preferably continuously. Step (II) is conducted only after a period corresponding to at least 10 times the residence time, preferably at least 30 times the residence time, more preferably at least 60 times the residence time and most preferably at least 90 times the residence time of phosgene (1) from exit from the apparatus 1000 to exit from the reaction stopping zone (4000) in the regular operation of the gas phase phosgenation plant (100) has elapsed, calculated from the moment from which M'(2) is zero. In this step, a gaseous inert gas stream (30) is maintained through the device 1100, the mixing zone (3100), the reaction zone (3200) and the reaction stopping zone (4000) (cf. also FIG. 3). The inert gas stream (30) consists of at least one gaseous inert substance (3), suitable inert substances being the same as described further up for the optional dilution of the phosgene in the gas stream (10).

The maintenance of the inert gas stream (30) in step (II) can be accomplished by (a) introducing an inert substance (3) which is preferably liquid at room temperature and standard pressure at a temperature $T_3$ less than the temperature desired for the inert gas stream (30) in step (II) into the apparatus 1000, heating it therein and then guiding it into the device 1100 and the other plant sections to be inertized. Preferably, the temperature of the inert gas stream (30) of step (II) is 200° C. to 600° C., more preferably 200° C. to 500° C. and most preferably 250° C. to 500° C. This embodiment is advantageous especially when the reaction mixture is diluted during the reaction in regular operation with the vapors of an inert substance (3) which is liquid at room temperature and standard pressure. It is possible to introduce the inert substance (3) in liquid form into the apparatus 1000 and to evaporate it only once therein. Inert substances (3) that are particularly suitable in variant (a) are inert solvents such as aromatic hydrocarbons, optionally having halogen substitution, for example chlorobenzene or dichlorobenzene (all isomers, preferably ortho-dichlorobenzene). In the apparatus 1000, the inert substance (3) is heated (i.e. evaporated in the case of introduction as a liquid) so as to obtain an inert gas stream (30) having a temperature $T_{30}$ of preferably 200° C. to 600° C., more preferably 200° C. to 500° C. and most preferably 250° C. to 500° C., and an absolute pressure $p_{30}$ of preferably 100 mbar to 3000 bar, more preferably 150 mbar to 2800 mbar and most preferably 200 mbar to 2500 mbar. The streams (3) and (30) do not differ in terms of chemical composition, but differ merely in terms of temperature and optionally pressure. After the stream (3) introduced into the apparatus 1000 has been heated, such that it leaves the apparatus 1000 in gaseous form, it is referred to as stream (30). If step (I) is executed according to variant (a), it is preferable also to execute step (II) according to variant (a).

It is also possible (b) to introduce an inert gas stream (30) at a temperature $T_{30}$ of preferably 200° C. to 600° C., more preferably 200° C. to 500° C. and most preferably 250° C. to 500° C., and an absolute pressure $p_{30}$ of preferably 100 mbar to 3000 mbar, more preferably 150 mbar to 2800 mbar and most preferably 200 mbar to 2500 mbar, directly into the apparatus 1000. In this embodiment, it is also possible to heat up the inert gas stream (30) introduced further in the apparatus 1000 within the scope of the above-defined temperature ranges. Alternatively, the inert gas stream (30) can also be fed directly into the device 1100. Variant (b), no matter what the configuration, is especially advantageous when the reaction mixture, during the reaction in regular operation, is being diluted with an inert substance already in gaseous form at room temperature and standard pressure, such as nitrogen, helium or argon. If step (I) is executed according to variant (b), it is preferable also to execute step (II) according to variant (b).

The effect of the performance of step (II) only after a period corresponding to at least 10 times the residence time, preferably at least 30 times the residence time, more preferably at least 60 times the residence time and most preferably at least 90 times the residence time of phosgene (1) from exit from the apparatus 1000 to exit from the reaction stopping zone (4000) in the regular operation of the gas phase phosgenation plant (100) has elapsed, calculated from the moment from which M'(2) is zero, is that residual amounts of unconverted amine (2) can be phosgenated.

In a preferred embodiment, the gas phase phosgenation plant (100) includes the workup section (5000). In that case, it is particularly preferable to use, in the regular operation of the gas phase phosgenation plant (100), as phosgene (1) in the phosgene gas stream (10), a mixture of fresh phosgene (1') and recycled phosgene (1") recovered in the devices 5100. This process regime additionally allows a particularly advantageous configuration of step (II) of the method of the invention to the effect that, after reduction of the amine mass flow rate M'(2) to zero, (II.a) first the supply of fresh phosgene (1') is stopped, and then (II.b) only after a period corresponding to at least 10 times the residence time, preferably at least 30 times the residence time, more preferably at least 60 times the residence time and most preferably at least 90 times the residence time of phosgene (1) from exit from the apparatus 1000 to exit from the reaction stopping zone (4000) in the regular operation of the gas phase phosgenation plant (100) has elapsed, calculated from the moment from which M'(2) is zero, the supply of recycled phosgene (1") is also stopped, such that the mass flow rate of phosgene M' (1) leaving the apparatus 1000 is zero, with maintenance during steps (II.a) and (II.b), as described further up, of a gaseous inert gas stream (30) through the device 1100, the mixing zone (3100), the reaction zone (3200) and the reaction stopping zone (4000), and optionally at least through parts of the device 5100.

Irrespective of whether the gas phase phosgenation plant (100) includes the workup section 5000, steps (I) and (II) are preferably conducted within less than 12 hours, preferably within less than 6 hours, more preferably within less than 3 hours and most preferably within less than 1 hour. Preferably, in steps (I) and (II), inert gas streams (30) of identical composition are used.

The inert gas stream (30) from (I) is (III) maintained at least for a period corresponding to three times, preferably 100 times, more preferably 200 times and most preferably 350 times the residence time of the inert gas stream (30) from entry into the mixing zone (3100) to exit from the reaction stopping zone (4000), calculated from the moment from which the mass flow rate of phosgene M'(1) leaving the apparatus 1000 is zero. In a preferred embodiment, at the same time, the inert gas stream from (II) is also maintained, in which case the residence time of the combined inert gas streams from (I) and (II) is crucial. Following step (III)—after cooling—it is optionally possible to open plant sections for maintenance operations.

The inert gas streams (30) from steps (I) and (II), after exiting from the reaction stopping zone (4000) or, if present, preferably after passing through at least parts of the workup devices 5100, are preferably discharged via an offgas discharge. In the preferred configuration of the process of the invention incorporating the workup section (5000), the inert gas streams (30) from steps (I) and (II) preferably pass through the scrubbing column (5110) and phosgene absorption column (5120) apparatuses described further up and are then discharged.

If two or more reaction zones (3200) are to be operated in parallel, it is preferable but not obligatory to shut them down successively, as described above. The dimensions of the secondary systems (such as the HCl absorption, phosgene absorption, any solvent workup or else offgas treatment) have to be such that the volumes of inert gas streams (30) required for shutdown are manageable.

If all the reactant pathways are shut down simultaneously, the above-described problems can occur. Phosgene can flow into the device 2100 (preferably amine nozzle) and can lead to blockages, baked-on polyurea, etc. In addition, the amount of phosgene at least briefly goes significantly below the phosgene excess desired at target mass flow rate $M'_{target}$ (2) in continuous production, again giving rise to by-products because the flow equilibria are disrupted and there is uncontrolled mixing. The residence time of the reactants in the reaction space is disrupted when both reactant streams are shut down simultaneously.

The inventive procedures in the shutdown of a gas phase phosgenation plant (100) therefore result in the following advantages for the restart:
i) Avoidance of blockages in the device 2100 (preferably the amine nozzle) and in the mixing zone (3100) and hence avoidance of any requirement for multiple startups because the plant had to be shut down to clean the device 2100 (preferably the amine nozzle).
ii) As a result of (i), saving of energy.
iii) Increasing the productivity of the gas phase phosgenation plant because there is no need for repeated shutdowns and restarts because of the occurrence of baked-on material and deposits.
iv) Increase in productivity and minimization of losses of feedstocks in the phosgene production.
v) Homogenization of production and increase in plant reliability because the thermal stress on the phosgenation plant (100) is reduced by the decrease in startup operations.
vi) Reduced by-product formation and shortened thermal stress on the product, accompanied by an increase in the relative yield.
vii) Avoidance or reduction of precipitates, baked-on material and blockages in the equipment (for example in the apparatus 2000 and the device 2100 or in the reaction zone prior to the stoppage of the reaction), accompanied by prolonging of the onstream time of the process.
viii) Lower level of waste after cleaning of the equipment (for example less polyurea to remove, avoidance of wash water that could trigger corrosion).
ix) Avoidance of off-spec material which can arise as a result of repeated poor startup and shutdown. Such poor-quality startup material thus does not have to be cut with good-quality polyisocyanate or even in the worst case incinerated.

Thus, the method of the invention enables, through avoidance of backmixing of phosgene (1) into the amine gas stream (20), during the shutdown of a gas phase phosgenation plant, a seamless restart of the plant and the subsequent workup of the crude isocyanate formed in a technically seamless manner with reduced or, in the ideal case, zero downtime with directly high end product quality. Complex cleaning operations during a shutdown can thus be avoided or at least be reduced in scope.

EXAMPLES

Content figures in ppm or % are parts by mass based on the total mass of the respective substance/stream of matter. General Conditions for the Preparation of Tolylene Diisocyanate (TDI) with a "Run-in" as Phase Production Plant (100) in Regular Operation
(See also FIG. 1 (simplified diagram))
Tolylenediamine (TDA) (2) is evaporated continuously in an amine evaporator (2000) together with nitrogen (3). The amine gas stream (20) thus obtained, containing 12 t/h of gaseous TDA (2), is injected continuously into the phosgenation reactor (3000) via a conduit (2100) with an amine nozzle present at the end thereof toward the phosgenation reactor (3000). The residence time of the TDA stream (20) from departure from the evaporator (2000) until exit from the amine nozzle is 5 seconds. At the same time, via a phosgene rectifier which is used as disclosed in EP-A-1 362 847, 61 t/h of a gaseous phosgene stream (10) are injected continuously into the phosgenation reactor (3000). The phosgene used is a mixture of fresh phosgene (1') and phosgene (1") recovered in the workup section (5000). In this case, the two reactants are mixed well, and there is no backmixing. The temperature of the gaseous TDA stream (20) at the mouth of the nozzle is 380° C. (TDA has a residence time of about 1 second at this temperature in the feed to the nozzle mouth). The gaseous phosgene (10) has a temperature of 320° C. when it leaves the phosgene rectifier, the residence time of the hot phosgene between the last phosgene superheater and phosgene rectifier being 2 seconds. The gaseous mixture of the streams (10) and (20) has a residence time of 8 seconds in the gas phase reactor (3000) and reacts at an absolute pressure of 1692 mbar to give a gaseous reaction mixture (40). The downstream reaction stopping zone (4000) comprises a two-stage "quench" in which the gaseous reaction mixture (40) is cooled down to 168° C. by spraying in ortho-dichlorobenzene (ODB), such that it is condensed and a mixture (60) of crude TDI and ODB collects in the bottoms vessel (4100). Excess phosgene, hydrogen chloride formed in the reaction and inerts are very substantially degassed from the bottoms vessel (4100) under these conditions, with reduction of the entrainment of TDI by means of internals. This residual process gas stream (50) is worked up (5100) to recover entrained TDI, phosgene and hydrogen chloride, as described in WO 2011/003532, page 11 lines 24 to 25. The mixture (60) from the bottoms vessel (4100) is worked up (5200) as described in EP 1 413 571 B1, giving TDI (4) in a mass flow rate of 15.6 t/h.

TDI (4) prepared in this way typically has a purity of >99.97% (gas chromatography, GC), a residual solvent content of ODB of <5 ppm (GC), a residual chlorine content of hydrolyzable chlorine of <10 ppm (titration in accordance with ASTM D4663), an acidity of bound chlorine of <5 ppm (titration in accordance with ASTM D5629), and the color number, measured as the Hazen number, is <15 (determined in accordance with DIN EN ISO 6271).

Comparative Example 1: Shutdown of a Gas Phase Phosgenation Plant (100) with Stoppage of the Phosgene Supply Before the Amine Supply A gas phase phosgenation plant (100) is operated at a production capacity of 15.6 t/h of TDI as described in the general conditions for preparation of TDI and then shut down as follows:
The phosgene feed is terminated, while the aminefeed is maintained for about a further 2 minutes. The amine TDA is no longer fully phosgenated during this period, and the intermediates and by-products formed block the mixing zone (3100), the reaction zone (3200) and the downstream reaction stopping zone ("quench", 4000). The pressure differential from entry of the TDA gas stream (20) and phosgene gas stream (10) reactants into the phosgenation reactor (3000) through the vapor gas exit of the bottom of the reaction stopping zone (4000) up to the TDI scrubbing column (5110) rises to 913 mbar within the short time during which the phosgene gas stream (10) was terminated and the amine gas stream (20) continued to run (about 2 minutes), rather than 10 mbar in standard operation. Cleaning of the reactor and its periphery has to be undertaken before a restart is possible.

Comparative Example 2: Shutdown of a Gas Phase Phosgenation Plant (100) with Simultaneous Stoppage of the Amine and Phosgene Supply The gas phase plant (100) is operated at a production capacity of 15.6 t/h of TDI as described in the general conditions for preparation of TDI and then shut down as follows:

The phosgene generator is shut down. Thereafter, the amine and phosgene supplies to the phosgenation reactor (3000) are stopped simultaneously. Subsequently, the phosgene reactor (3000) is inertized with nitrogen until the phosgenation reactor and its pipeline periphery have been freed of reactants and product.

After a brief reaction stoppage, the amine evaporator including the downstream heat exchanger (2000) and the devices 2100 including the amine nozzle are charged with nitrogen, with a set temperature of 380° C. The phosgenation reactor (3000) is reactant- and product-free and inertized with hot nitrogen. The amine evaporation in the amine evaporator is started, such that TDA evaporates at 300° C. Subsequently, the TDA is heated stepwise to 380° C. in further heat exchangers and injected into the phosgenation reactor (3000) through the amine nozzle as a gaseous TDA stream (20) at a pressure of 1691 mbar (absolute). Within 45 minutes, the mass flow rate of TDA (2) which is introduced into the phosgenation reactor (3000) is increased continuously from 0 t/h to 12 t/h. Shortly before the TDA gas stream (20) passes through the amine nozzle into the phosgenation reactor (3000), the phosgene pathway is opened and a phosgene gas stream (10) is injected into the phosgenation reactor (3000) with a mass flow rate of 61 t/h and a temperature of 320° C. and a pressure of 1691 mbar (absolute) at the reactor inlet. The plant attains the regular operating state after 45 minutes. After 7 days, the plant has to be shut down because the pressure differential from entry of the TDA gas stream (20) and phosgene gas stream (10) reactants into the phosgenation reactor (3000) through the vapor gas exit of the bottom of the reaction stopping zone (4000) up to the TDI scrubbing column (5110) rises to 793 mbar over time, rather than 10 mbar in standard operation, and the energy required to evaporate phosgene and TDA and transfer the gas streams (10) and (20) into the phosgenation reactor (3000) can barely be raised (the boiling temperature of TDA (2) limits the evaporator capacity with increasing pressure). After shutdown and opening of the plant, severe polyurea-containing deposits are found at the exit of the amine nozzle, along the surface of the reactor space and on the surfaces of the quenches.

Comparative Example 3: Shutdown of a Gas Phase Phosgenation Plant (100) with Shutdown of the Amine Supply Before the Phosgene Supply, but without Inert Gas Purging of the Amine Supply Devices (Backflow of Phosgene into Amine Nozzle)

A gas phase production plant (100) is operated at a production capacity of 15.6 t/h of TDI as described in the general conditions for preparation of TDI and then shut down as follows:

The amine supply to the phosgenation reactor (3000) is stopped by closing the reactant-guiding pipeline (constituent of device 2100) beyond the amine evaporator (2000). No inert gas purging of the device 2100 is conducted. Thereafter, the phosgene reactor is shut down and so the supply of fresh phosgene (1') is stopped. After 15 minutes (corresponding to about 112 times the residence time of phosgene (1) from exit from the apparatus 1000 to exit from the reaction stopping zone (4000) in the regular operation of the gas phase phosgenation plant (100)), the phosgene circuit is run down by also stopping the supply of recycled phosgene (1") to the phosgenation reactor (3000). Subsequently, the phosgenation reactor (3000) is inertized with nitrogen.

After a brief shutdown, circulation of phosgene is built up by running recycled phosgene (1") from the workup (5100) of the vapors (50) from the reaction stopping zone (4000) at a temperature of 320° C. through the phosgenation reactor (3000), the reaction stopping zone (4000), back to the workup. In the reaction stopping zone (4000), during this time, only the second quench in flow direction of the reaction mixture (40) is in operation, as a result of which the phosgene stream is cooled down. In this phosgene circuit, 61 t/h of phosgene are circulated. During this time, the conduit 2100 including the amine nozzle are purged with a nitrogen gas stream (30). As soon as the phosgenation reactor (3000) has been heated to 320° C., amine evaporation is started by running liquid TDA (2) preheated to 220° C. together with nitrogen into the amine evaporator (2000), evaporating it therein with the aid of a heat exchanger at 300° C. and then heating it to 410° C. with a further heat exchanger. The TDA stream (20) thus obtained is injected at an absolute pressure of 1654 mbar through the amine nozzle into the phosgenation reactor (3000). The amount of TDA (2) which is introduced into the phosgenation reactor (3000) during the startup of the gas phase phosgenation plant (i.e. until the amine mass flow rate reaches $M'_{target}(2)$, which happens after 45 minutes) is increased continuously from 0 t/h to 12 t/h, the operating pressure in the phosgenation reactor (3000) at the end of the startup being 1641 mbar (absolute). The first quench in flow direction of the reaction mixture (40) is put into operation shortly before TDA gas stream (20) for the first time leaves the amine nozzle in the direction of the phosgenation reactor (3000) in the course of startup. The phosgene consumed after the startup of the plant is replaced by a mixture of fresh phosgene (1') and phosgene recovered in the workup (1"). After 60 minutes, 15.6 t/h of TDI (4) leave the last distillation column of the workup stage.

After the startup, the pressure differential between amine evaporation (2000) and the phosgenation reactor (3000) increases ever further. After 3 hours, the phosgenation reactor (3000) has to be shut down because the operating pressure at the amine nozzle has risen to 2.5 bar (absolute). After shutdown and opening of the plant, charred residues are found in the exit orifice of the amine nozzle and in the pipeline leading to the amine nozzle. This is attributable to backflows of phosgene into the device 2100 during the startup phase, forming TDI deposits which block the exit orifice of the amine nozzle.

Comparative Example 4: Startup of a Gas Phase Phosgenation Plant (100) with Stoppage of the Amine Supply (while Maintaining the Inert Gas Purge of the Amine Feed Devices (Prevention of Phosgene Backflow into Amine Nozzle)) Before the Phosgene Supply, but with Too Short a Postreaction Time (Residence Time) with Phosgene The gas phase phosgenation plant (100) is operated at a production capacity of 15.6 t/h of TDI as described in the general conditions for preparation of TDI and shut down as follows:

The amine supply to the phosgenation reactor (3000) is stopped by closing the reactant-guiding pipeline (constituent of device 2100) beyond the amine evaporator (2000). During this time, a gaseous nitrogen stream is maintained through the device 2100, the mixing zone (3100), the reaction zone (3200), the reaction stopping zone (4000) and parts of the device 5100 (scrubbing column 5120 and phosgene absorption column 5120, neither shown in FIG. 1) (step (I) of the method of the invention). After the amine mass flow rate M'(2) has been reduced to zero, the phosgene generator is shut down, and so the supply of fresh phosgene (1') is terminated (step (II.a) of the method of the invention). After 30 seconds (corresponding to about 4 times the residence time of phosgene (1) from exit from the apparatus 1000 to exit from the reaction stopping zone (4000) in the regular operation of the gas phase phosgenation plant (100)), the phosgene circuit is run down by also stopping the supply of recycled phosgene (1") to the phosgenation reactor (3000) (step (II.b) of the method of the invention). During the whole time, the device 1100, the reactor (3000), the reaction stopping zone (4000) and parts of the device 5100 (scrubbing column 5120 and phosgene absorption column 5120, neither shown in FIG. 1) are purged with nitrogen, which leaves the device 5100 by discharge from the phosgene absorption column (5120). After the phosgene circulation has been terminated, the nitrogen streams from steps (I), (II.a) and (II.b), are maintained for another 1 hour (corresponding to about 400 times the residence time of the combined inert gas streams (30), from entry into the mixing zone (3100) to exit from the reaction stopping zone (4000)) (step (III) of the method of the invention), after which the phosgenation reactor (3000) has been freed of the reactants and product.

After a maintenance shutdown of one day in another section of the plant, the gas phase phosgenation plant is started up again as described in example 3.

At the end of the startup, the operating pressure in the phosgenation reactor (3000) is 1651 mbar (absolute). After 13 days, the plant has to be shut down because the pressure differential from entry of the TDA gas stream (20) and phosgene gas stream (10) reactants into the phosgenation reactor (3000) through the vapor gas exit of the bottom of the reaction stopping zone (4000) up to the TDI scrubbing column (5110) rises to 803 mbar over time, rather than 10 mbar in standard operation, and the energy required to evaporate phosgene and TDA and transfer the gas streams (10) and (20) into the phosgenation reactor (3000) can barely be raised (the boiling temperature of TDA (2) limits the evaporator capacity with increasing pressure). After shutdown and opening of the plant, severe polyurea-containing deposits are found at the exit of the amine nozzle, along the surface of the reactor space and on the surfaces of the quenches.

Example 5 (Inventive)

The gas phase phosgenation plant (100) is operated at a production capacity of 15.6 t/h of TDI as described in the general conditions for preparation of TDI and shut down as follows:

The amine supply to the phosgenation reactor (3000) is stopped by closing the reactant-guiding pipeline (constituent of device 2100) beyond the amine evaporator (2000). During this time, a gaseous nitrogen stream is maintained through the device 2100, the mixing zone (3100), the reaction zone (3200), the reaction stopping zone (4000) and parts of the device 5100 (scrubbing column 5120 and phosgene absorption column 5120, neither shown in FIG. 1) (step (I) of the method of the invention). After the amine mass flow rate M'(2) has been reduced to zero, the phosgene generator is shut down, and so the supply of fresh phosgene (1') is terminated (step (II.a) of the method of the invention). After 15 minutes (corresponding to about 112 times the residence time of phosgene (1) from exit from the apparatus 1000 to exit from the reaction stopping zone (4000) in the regular operation of the gas phase phosgenation plant (100)), the phosgene circuit is run down by also stopping the supply of recycled phosgene (1") to the phosgenation reactor (3000) (step (II.b) of the method of the invention). During the whole time, the device 1100, the reactor (3000), the reaction stopping zone (4000) and parts of the device 5100 (scrubbing column 5120 and phosgene absorption column 5120, neither shown in FIG. 1) are purged with nitrogen, which leaves the device 5100 by discharge from the phosgene absorption column (5120). After the phosgene circulation has been terminated, the nitrogen streams from steps (I), (II.a) and (II.b), are maintained for another 1 hour (corresponding to about 400 times the residence time of the combined inert gas streams (30), from entry into the mixing zone (3100) to exit from the reaction stopping zone (4000)) (step (III) of the method of the invention), after which the phosgenation reactor (3000) has been freed of the reactants and product.

After a maintenance shutdown of one day in another section of the plant, the gas phase phosgenation plant is started up again as described in example 3.

In example 5, no blockage of the amine nozzle and no occurrence of deposits in the phosgenation reactor are observed during the shutdown. The plant can be restarted without any problems and operated over a further phosgenation cycle of several months. The occurrence of unwanted by-products such as polyureas etc. is significantly reduced, and the startup material has high quality, such that it need not be cut with TDI produced at a later time.

The invention claimed is:

1. A method of operating a gas phase phosgenation plant that is configured to produce an isocyanate by reacting an amine with phosgene in a stoichiometric excess in relation to the primary amino groups of the amine to give the corresponding isocyanate, and that comprises at least
   (i) an apparatus for providing a gaseous phosgene stream, which optionally comprises an inert substance in addition to phosgene,
   (ii) an apparatus for providing a gaseous amine stream, which optionally comprises an inert substance in addition to amine,
   (iii) a mixing zone for mixing the gaseous phosgene stream and the gaseous amine stream, with the mixing zone being connected by connecting devices for the phosgene stream and for the amine stream to the apparatus for providing a gaseous phosgene stream and the apparatus for providing a gaseous amine stream,
   (iv) a reaction zone arranged downstream of the mixing zone for further conversion of the previously mixed streams and,
   (v) a reaction stopping zone arranged downstream of the reaction zone to end the reaction,
   and optionally
   (vi) a workup section which comprises devices for recovery and recycling of unconverted phosgene and devices for obtaining the isocyanate prepared in pure form,
   wherein
   the gas phase phosgenation plant is shut down by:
   (I) reducing the amine mass flow rate introduced into the apparatus for providing a gaseous amine stream to zero, while maintaining a gaseous inert gas stream through the connecting device for the amine stream, the mixing zone, the reaction zone and the reaction stopping zone;

(II) reducing the mass flow rate of phosgene leaving the apparatus for providing a gaseous phosgene stream to zero, while maintaining a gaseous inert gas stream through the connecting device for the phosgene stream, the mixing zone, the reaction zone and the reaction stopping zone only after a period corresponding to at least 10 times the residence time of phosgene from exit from the apparatus for providing a gaseous phosgene stream to exit from the reaction stopping zone in the regular operation of the gas phase phosgenation plant has elapsed, calculated from the moment from which the amine mass flow rate is zero; and (III) maintaining at least the inert gas stream from (I), at least for a period corresponding to three times the residence time of the inert gas stream from entry into the mixing zone to exit from the reaction stopping zone, calculated from the moment from which the mass flow rate of phosgene leaving the apparatus for providing a gaseous phosgene stream is zero.

2. The method as claimed in claim 1, in which the gas phase phosgenation plant includes the workup section and in which, in the regular operation of the gas phase phosgenation plant, the phosgene in the phosgene gas stream comprises a mixture of fresh phosgene and recycled phosgene recovered in the recovery and recycling devices.

3. The method as claimed in claim 2, in which, after the reduction of the amine mass flow rate introduced into the apparatus for providing a gaseous amine stream to zero has been completed, (II.a) stopping the supply of fresh phosgene first, and then
(II.b) stopping the supply of recycled phosgene only after a period corresponding to at least 10 times the residence time of phosgene from exit from the apparatus for providing a gaseous phosgene stream to exit from the reaction stopping zone in the regular operation of the gas phase phosgenation plant has elapsed, calculated from the moment from which the reduction of the amine mass flow rate to zero has been completed, such that the mass flow rate of phosgene leaving the apparatus for providing a gaseous phosgene stream is zero,
with maintenance during (II.a) and (II.b) of a gaseous inert gas stream through the connecting device for the phosgene stream, the mixing zone, the reaction zone and the reaction stopping zone.

4. The method as claimed in claim 1, in which the compositions and mass flow rates of the gaseous phosgene stream and the gaseous amine stream and in operation of the gas phase phosgenation plant in regular operation are matched to one another such that phosgene in the gaseous phosgene stream is present in a stoichiometric excess in relation to the primary amino groups of the amine in the gaseous amine stream in an amount that is at least 150% of the theoretically required amount.

5. The method as claimed in claim 1, in which, in (I), the amine mass flow rate introduced into the apparatus for providing a gaseous amine stream is reduced to zero continuously or in stages.

6. The method as claimed in claim 3, in which, in (II.a), the supply of fresh phosgene is reduced to zero continuously or in stages.

7. The method as claimed in claim 1, in which the connecting device for the phosgene stream comprises a nozzle.

8. The method as claimed in claim 1, in which the connecting device for the amine stream comprises a nozzle.

9. The method as claimed in claim 1, in which the connecting devices for the phosgene stream and for the amine stream comprise a common nozzle apparatus.

10. The method as claimed in claim 1, in which the reaction stopping zone is operated below the boiling temperature of the isocyanate and above the breakdown temperature of the carbamoyl chloride which corresponds to the amine by contacting the gaseous process product exiting from the reaction zone with an inert solvent.

11. The method as claimed in claim 10, in which the reaction stopping zone is taken out of operation no earlier than when the mass flow rate of phosgene leaving the apparatus for providing a gaseous phosgene stream is zero.

12. The method as claimed in claim 1, in which the inert gas stream in (I) is introduced into the apparatus for providing a gaseous amine stream or into the connecting device for the amine stream, and in which the inert gas stream in (II) is introduced into the apparatus for providing a gaseous phosgene stream or the connecting device for the phosgene stream.

13. The method as claimed in claim 1, in which the inert gas stream in (I) is obtained by heating an inert substance which is introduced into the apparatus for providing a gaseous amine stream, and in which the inert gas stream in (II) is obtained by heating an inert substance which is introduced into the apparatus for providing a gaseous phosgene stream.

14. The method as claimed in claim 1, in which the inert gas streams in (I) and in (II) each independently have a temperature in the range from 200° C. to 600° C.

15. The method as claimed in claim 1, in which the amine is selected from the group consisting of isophoronediamine, hexamethylenediamine, bis(p-aminocyclohexyl)methane, tolylenediamine and diphenylmethanediamine.

16. The method as claimed in claim 1, in which the mass flow rate of phosgene leaving the apparatus for providing a gaseous phosgene stream is reduced to zero only after a period corresponding to at least 30 times the residence time of phosgene from exit from the apparatus for providing a gaseous phosgene stream to exit from the reaction stopping zone in the regular operation of the gas phase phosgenation plant (100) has elapsed, calculated from the moment from which the amine mass flow rate introduced into the apparatus for providing a gaseous amine stream is zero.

17. The method as claimed in claim 1, in which (III) the inert gas streams from (I) and (II) are maintained at least for a period corresponding to 100 times the residence time of the inert gas stream from entry into the mixing zone to exit from the reaction stopping zone, calculated from the moment from which the mass flow rate of phosgene leaving the apparatus for providing a gaseous phosgene stream is zero.

18. The method as claimed in claim 13 in which the inert gas stream in (I) is obtained by heating an inert substance which is liquid at room temperature and standard pressure and is introduced into the apparatus for providing a gaseous amine stream, and in which the inert gas stream in (II) is obtained by heating an inert substance, which is liquid at room temperature and standard pressure and is introduced into the apparatus for providing a gaseous phosgene stream.

* * * * *